United States Patent [19]
Chaturvedula et al.

[11] Patent Number: 5,892,024
[45] Date of Patent: Apr. 6, 1999

[54] BIFUNCTIONAL NUCLEOSIDES, OLIGOMERS THEREOF, AND METHODS OF MAKING AND USING THE SAME

[75] Inventors: Prasad Venkata Chala Chaturvedula, Exton; Ashis Kumar Saha, Frazer, both of Pa.

[73] Assignee: Sanofi, Paris Cedex, France

[21] Appl. No.: 816,708

[22] Filed: Mar. 13, 1997

Related U.S. Application Data

[63] Continuation of Ser. No. 359,798, Dec. 20, 1994, abandoned, which is a continuation of Ser. No. 41,310, Mar. 31, 1993, abandoned.

[51] Int. Cl.$^6$ .................. C07H 19/067; C07H 19/073; C07H 19/167; C07H 19/173
[52] U.S. Cl. .................. 536/27.6; 536/24.5; 536/25.3; 536/27.81; 536/28.5; 536/28.53; 536/28.54
[58] Field of Search .................. 435/6, 375; 514/44; 536/21.3, 24.3, 24.5, 25.3, 27.21, 27.6, 27.81, 28.4, 28.5, 28.53, 28.54

[56] References Cited

U.S. PATENT DOCUMENTS 4,841,039  6/1989  Chu et al. .................. 536/28.2

FOREIGN PATENT DOCUMENTS

| 317128 | 5/1989 | European Pat. Off. . |
|---|---|---|
| 322384 | 6/1989 | European Pat. Off. . |
| WO/9202534 | 2/1992 | WIPO . |
| WO/9205186 | 4/1992 | WIPO . |
| WO/9220822 | 11/1992 | WIPO . |
| WO/9220823 | 11/1992 | WIPO . |

OTHER PUBLICATIONS

Baker et al. "An evaluation of certain chain–extended analogues . . . " J. Med. Chem. 26, 1530–1534, 1983.
Kurihara et al. "Improved synthesis of 5'–deoxy–5'–adenosineacetic acid" Chem. Pharm. Bull. 31, 2126–2129, 1983.
Lin et al. "Synthesis and biological activity of several amino analogues of thymidine" J. Med. Chem 21, 109–112, 1978.
Montgomery and Thomas. "Diazomethyl ketone derivatives of pyrimidine nucleosides" J. Org. Chem. 46, 594–598, 1981.
Montgomery et al. Analogs of 5'–deoxy–5'–(methylthio)adenosine. J. Med. Chem. 17:1197–1207, 1974.
Chu et al. Synthesis of Pyrimidine 3'–allyl–2', 3'–dideoxyribonucleosides by free radical coupling. J. Org. Chem. 54: 2767–2769, 1989.
Jones. Preparation of protected deoxyribonucleosides. In "Oligonucleotide Synthese" M. J. Gait, ed. IRL Press, Washington, DC. pp. 23–34, 1984.
Corey, D. R, et al. Generation of a catalytic sequence–specific hybrid DNase. Biochemistry 28(21): 8277–8286, 1989.
Garegg, P. J., et al. Nucleoside H–phosphonates. III. Chemical synthesis of oligodeoxynucleotides by the hydrogen-phosphonate approach. Tetrahedron Letts. 27(34): 4051–4054, 1986.
Froehler, B. C., et al, Nucleoside H–phosphonates: Valuable intermediates in the synthesis of deoxyoligonucleotides. Tetrahedron Letts. 27(4): 469–472, 1986.
Chemical Abstracts, 111:78534g (1989).
Chemical Abstracts, 114:122934a (1991).
Chemical Abstracts, 78:148172p (1973).

*Primary Examiner*—George C. Elliott
*Assistant Examiner*—Thomas G. Larson
*Attorney, Agent, or Firm*—Mary P. Bauman; Michael D. Alexander

[57] ABSTRACT

Disclosed are novel bifunctional nucleoside analogs and oligonucleosides of 3–4 bases (trimers and tetramers) and longer containing at least two consecutive internucleoside linkages of two carbon-one nitrogen atom or two carbon-one oxygen atom (3'-NCC-5', 3'-CNC-5', 3'-OCC-5') internucleoside linkages. The bifunctional nucleosides are useful for preparing the trimers and tetramers, which, in turn, are useful, together with the nucleosides, in preparing oligonucleosides as well as chimeric oligonucleotide analogs, preferably antisense oligonucleosides and oligonucleotide analogs, of 6 to about 60 bases having at least two consecutive internucleoside linkages of two carbon atoms and one nitrogen atom or 2 carbon atoms and one oxygen atom in the oligonucleoside backbone.

3 Claims, No Drawings

5,892,024

BIFUNCTIONAL NUCLEOSIDES, OLIGOMERS THEREOF, AND METHODS OF MAKING AND USING THE SAME

This application is a continuation of application Ser. No. 08/359,798 filed Dec. 20, 1994, now abandoned, which is a continuation of application Ser. No. 08/041,310 filed Mar. 31, 1993, now abandoned.

FIELD OF THE INVENTION

The present invention relates to novel bifunctional nucleosides and to bifunctional trimers, tetramers (and longer oligomers thereof) that are useful for preparing oligonucleoside compounds having oligonucleoside sequences of from 4 to about 60 bases having a continuous backbone of internucleoside linkages consisting of two carbon atoms and one nitrogen atom or two carbon atoms and one oxygen atom. The invention also relates to the oligonucleosides so produced as well as to mixed oligonucleotides (chimeric oligonucleotide analogs) of up to 60 or more bases comprising the above-described oligonucleoside sequences interspersed with nucleoside sequences wherein the nucleosides are linked by natural phosphodiester internucleoside linkages. The present invention also involves a process for preparing the above-described oligonucleoside and chimeric oligonucleotide analog compounds using the dimeric nucleoside compounds of this invention, this process comprising joining a 5'-nucleoside, a middle, bifunctional, unit and a 3' nucleoside, by conventional synthetic organic methods known in the art, to produce various oligomers which may be useful as antisense compounds.

BACKGROUND OF THE INVENTION

An antisense compound binds to or hybridizes with a nucleotide sequence in a nucleic acid (RNA or DNA) to inhibit the function (or synthesis) of the nucleic acid. Because they can hybridize with both RNA and DNA, antisense compounds can interfere with gene expression at the level of transcription, RNA processing or translation. The resulting interference leads to an inhibition of the synthesis of the protein encoded by the nucleic acid, such as the proteins of the tissues, various cellular growth factors, growth factor receptors, and oncogenes.

As discussed, e.g., in Klausner, A., *Biotechnology*, 8:303–304 (1990), the development of practical applications of antisense technology is hampered by a number of technical problems. Thus, natural, phosphate-linked antisense oligomer compounds are susceptible to rapid degradation by nucleases that exist in target cells and elsewhere in the body; such as exonucleases, which act on either the 3' or the 5' terminus of the nucleic acid, and endonucleases, which cleave the nucleic acid at internal phosphodiester linkages between individual nucleosides. As a result of such nuclease action, the effective half life of many administered antisense compounds is very short, necessitating the use of large, frequently administered, doses.

The high cost of producing antisense DNA or RNA on currently available DNA synthesizers is another problem. Armstrong, L., Business Week, Mar. 5, 1990, page 89, estimated the cost of producing one gram of antisense DNA to be about $100,000.

There is also a problem regarding delivery of antisense agents to targets within the body (and cell). Thus, antisense agents targeted to messenger RNA must permeate the plasma membrane and antisense agents targeted to genomic DNA must permeate both the plasma membrane and the nuclear membrane to gain access to the nucleus. The consequent need for increased hydrophobicity to enhance membrane permeability must be balanced against the need for increased hydrophilicity (water solubility) in body fluids such as the plasma and cell cytosol.

Also, oligonucleotide compounds such as antisense DNA are susceptible to steric reconfiguration around chiral phosphorous centers. This results in stability problems, too, whether the compounds are free within the body or hybridized to target nucleic acids.

To overcome the stability and drug delivery limitations, various oligonucleotide analogs have been investigated. In order to be of practical utility, such analogs should have good cell penetration properties, be resistant to nuclease degradation, have good sequence specific hybridization to target nucleic acids, and be synthesized by chemical methods that are not too difficult or costly.

Recent efforts to overcome the foregoing problems and prepare antisense compounds that are stable, nuclease resistant, relatively inexpensive to manufacture and which can be delivered to and hybridized with nucleic acid targets throughout the body have involved synthesizing oligonucleotide analogs that consist of oligonucleoside sequences with internucleoside linkages that differ from the 'normal' internucleoside phosphodiester linkage, either by introducing modifications in the phosphodiester structure or by using non-phosphate internucleoside linkages that approximate the length and orientation of the normal phosphodiester internucleoside linkage. Uhlman, E. and Peyman, A., *Chemical Reviews*, 9(4):544–584 (1990).

Among the modified phosphodiester linkages that have been reported are phosphorothioates, alkylphosphotriesters, methylphosphonates and alkylphosphoramidates. Also, a variety of non-ionic oligonucleoside sequences containing non-phosphate internucleoside linkages, such as carbonate, acetate, carbamate, sulfone, sulfoxide, sulfonamide and dialkyl- or diaryl- silyl derivatives have been synthesized and reported. More recently, chimeric oligonucleotide analogs comprising nucleoside linkages containing two carbon atoms and one nitrogen atom or one oxygen atom, as well as those containing three carbon atoms, have been reported. See, e.g., International Patent Publication WO 9202534.

SUMMARY OF THE INVENTION

The present invention provides novel bifunctional nucleoside analogs and oligonucleosides of three to four bases (trimers and tetramers) and longer, containing continuous stretches of two carbon-one nitrogen atom and two carbon-one oxygen atom (3'-NCC-5', 3'-CNC-5', 3'-OCC-5') internucleoside linkages. The bifunctional nucleosides of the invention are useful for preparing the trimers and tetramers of the invention, which, in turn, are useful, together with the nucleosides, in preparing the oligonucleosides of the invention as well as chimeric oligonucleotide analogs, preferably antisense oligonucleosides and oligonucleotide analogs, of 6 to about 60 bases having at least two consecutive internucleoside linkages of two carbon atoms and one nitrogen atom or 2 carbon atoms and one oxygen atom in the oligonucleoside backbone.

As used herein, the term 'oligonucleotide' means nucleic acid compounds which contain only 'natural' phosphodiester internucleoside linkages. On the other hand, the term 'chimeric oligonucleotide analogs' means compounds that comprise sequences containing both oligonucleoside linkages and oligonucleotide linkages. By the term 'oligonucleosides,' is meant oligonucleotide analogs that contain only synthetic (as opposed to the naturally occurring phosphodiester) internucleoside linkages.

More particularly, the present invention provides novel nucleoside analogs of Formula I below and oligonucleosides of Formula II below:

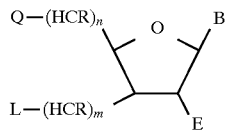

Formula I

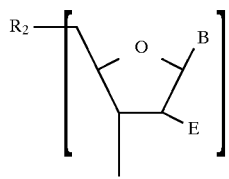

Formula II

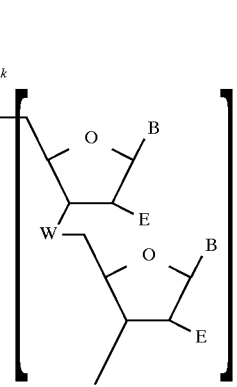
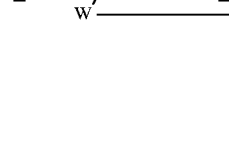
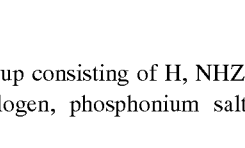

wherein,

Q is selected from the group consisting of H, NHZ, OZ, SZ, CHO, COOR, halogen, phosphonium salt and phosphonate;

L is selected from the group consisting of NHZ, OZ, SZ, CHO, COOR, halogen, phosphonium salt and phosphonate;

Q-(HCR)$_n$- and L-(HCR)$_m$ can also be replaced independently by:

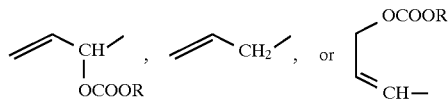

each R is independently selected from the group consisting of H, lower alkyl, lower alkenyl, aryl, and acyl;

each Z is independently selected from the group consisting of H, lower alkyl, lower alkenyl, aryl, acyl, and protecting groups for O-, S-, and N-;

each E is independently selected from the group consisting of H, and OZ;

each $R_2$ is independently selected from the group consisting of P(O$_2$)OZ, OZ, NHZ, SZ, CHRCHRHZ and CR=CRNHZ;

m is 0 or an integer from 1 to 4;

n is an integer from 1 to 5;

each B is independently select from the group consisting of adenine, cytosine, guanine, thymine, uracil or a modification thereof that does not substantially interfere with the affinity of an oligonucleoside or chimeric oligonucleotide analog for its antisense counterpart wherein the bases are selected from the group consisting of adenine, cytosine, guanine, thymine and uracil;

W is D-D-D where each D is independently (HCR), oxygen or NHR, with the proviso that two of the D's of each W are (HCR) and the third D is —O or —NHR;

j is an integer from 1 to 60;

k is 0 or an integer from 1 to 60; and q is 0 or an integer from 1 to 60, with the proviso that the sum of j+k+q is from 3 to about 60.

The present invention also provides chimeric oligonucleotide analogs having the structure of Formula II above wherein each of R, Z, E, $R_2$, $R_1$, m, n, B, W, j, k and q is as defined above, with the proviso that at least one W is a natural phosphodiester linkage and at least two contiguous W's are D-D-D.

The present invention also provides a method of synthesizing compounds consisting of nucleoside sequences of from 3 to 60 bases or more having a series of at least two sequential internucleoside linkages of two carbon atoms and one nitrogen atom or two carbon atoms and one oxygen atom, this method comprising joining a 5'-nucleoside, a middle, bifunctional unit of Formula I, and a 3'-nucleoside to produce oligomers of Formula II, which may be useful as antisense oligonucleosides or as components of larger oligonucleosides which may also contain natural phosphodiester internucleoside linkages or other suitable internucleoside linkages known to those skilled in the art, this method employing the compounds of the present invention, preferably as reagents in an automated gene synthesizer.

DETAILED DESCRIPTION OF THE INVENTION

The nucleoside analogs of the present invention have the Formula I:

wherein:

Q is selected from the group consisting of H, NHZ, OZ, SZ, CHO, COOR, halogen, phosphonium salt and phosphonate;

L is selected from the group consisting of NHZ, OZ, SZ, CHO, COOR, halogen, phosphonium salt and phosphonate;

$Q\text{-}(HCR)_n\text{-}$ and $L\text{-}(HCR)_m$ can also be replaced independently by:

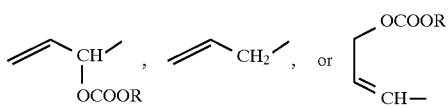

each R is independently selected from the group consisting of H, lower alkyl, lower alkenyl, aryl, and acyl;

each Z is independently selected from the group consisting of H, lower alkyl, lower alkenyl, aryl, acyl, and protecting groups for O-, S-, and N-;

each E is independently selected from the group consisting of H, and OZ;

m is 0 or an integer from 1 to 4;

n is an integer from 1 to 5; and each B is independently select from the group consisting of adenine, cytosine, guanine, thymine, uracil or a modification thereof that does not substantially interfere with the affinity of an oligonucleoside or chimeric oligonucleotide analog for its antisense counterpart wherein the bases are selected from the group consisting of adenine, cytosine, guanine, thymine, uracil or a naturally occurring modification thereof.

The trimeric, tetrameric and longer oligonucleosides of this invention have the Formula II below:

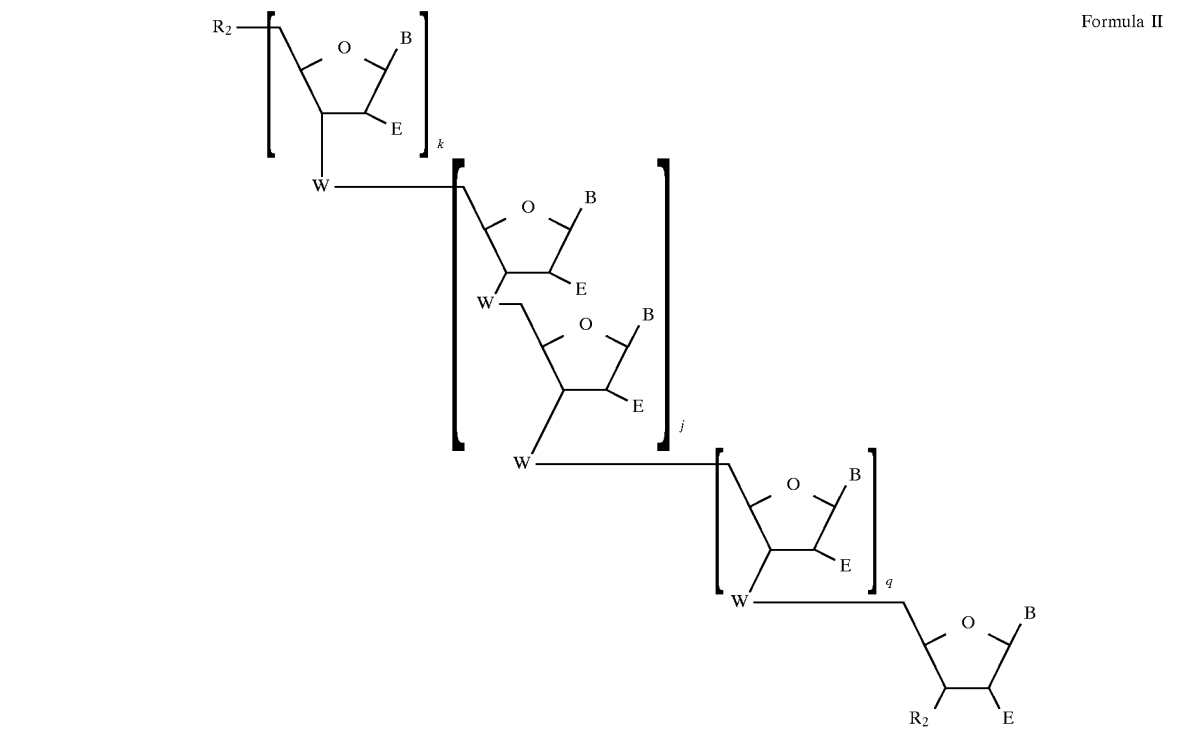

wherein:
   each $R_2$ is independently selected from the group consisting of $P(O_2)OZ$, OZ, NHZ, SZ, CHRCHRNHZ and CR=CRNHZ;
   each R is independently selected from the group consisting of H, lower alkyl, lower alkenyl, aryl, and acyl;
   each Z is independently selected from the group consisting of H, lower alkyl, lower alkenyl, aryl, acyl, and protecting groups for O-, S-, and N-;
   each E is independently selected from the group consisting of H, and OZ;
   each B is independently select from the group consisting of adenine, cytosine, guanine, thymine, uracil or a modification thereof that does not substantially interfere with the affinity of an oligonucleoside or chimeric oligonucleotide analog for its antisense counterpart wherein the bases are selected from the group consisting of adenine, cytosine, guanine, thymine, uracil or a naturally occurring modification thereof;
   W is D-D-D where each D is independently (HCR), oxygen or NHR, with the proviso that two of the D's of each W are (HCR) and the third D is —O or —NHR;
   j is an integer from 1 to 60;
   k is 0 or an integer from 1 to 60; and
   q is 0 or an integer from 1 to 60, with the proviso that the sum of j+k+q is from 3 to about 60.

The chimeric oligonucleotide analogs of the present invention have the structure of Formula II above wherein each of R, Z, E, $R_2$, $R_1$, m, n, B, W, j, k and q is as defined above, except that at least one W is a natural phosphodiester linkage and at least two contiguous W's are D-D-D as defined above.

As employed above and throughout the disclosure, the following terms, unless otherwise indicated, shall be understood to have the following meanings:

"Alkyl" means a saturated aliphatic hydrocarbon which may be either straight- or branched-chain. Preferred groups have no more than about 12 carbon atoms and may be methyl, ethyl and structural isomers of propyl, butyl, pentyl, hexyl, heptyl, octyl, nonyl, decyl, undecyl and dodecyl.

"Lower alkyl" means an alkyl group as above, having 1 to 7 carbon atoms. Suitable lower alkyl groups are methyl, ethyl, n-propyl, isopropyl, butyl,, tert-butyl, n-pentyl, neopentyl, n-hexyl, and n-heptyl.

"Aryl" means phenyl, naphthyl, substituted phenyl and substituted naphthyl.

"Substituted phenyl (or naphthyl)" means a phenyl (or naphthyl) group in which one or more of the hydrogens has been replaced by the the same or different substituents selected from halo, lower alkyl, nitro, amino, acylamino, hydroxyl, lower alkoxy, aryl, heteroaryl, lower alkoxy, alkylsulfonyl, and trifluoromethyl.

"Heteroaryl group" means groups such as pyridyl, furyl, thienyl, or imidazolyl.

"Substituted heteroaryl" means a heteroaryl group in which one or more of the hydrogens has been replaced by the the same or different substituents selected from halo, lower alkyl, nitro, amino, acylamino, hydroxyl, lower alkoxy, aryl, heteroaryl, lower alkoxy, alkylsulfonyl, and trifluoromethyl.

"Lower alkenyl" means an unsaturated aliphatic hydrocarbon having 2 to 8 carbon atoms, such as ethylene, propylene, butylene, isobutylene, etc., including all structural and geometrical isomers thereof.

"Halo" means bromo, chloro or fluoro.

An "O-, S-, or N-protecting group" is a radical attached to an oxygen, sulfur, or nitrogen atom, respectively, which radical serves to protect the oxygen, sulfur, or nitrogen functionality against undesired reaction. Such protecting groups are well known in the art; many are described in "The Peptides." E. Gross and J. Meienhofer, Eds. Vol 3 Academic Press, NY (1981). The N-protecting groups can be N-acyl, N-alkoxycarbonyl, N-arylmethoxy-carbonyl, trifluoromethylacyl and N-arylsulfonyl protecting groups. Suitable O-protecting groups include benzyl, tert-butyl, methyl, tosyl, dimethoxytrityl, tert-butyl-dimethylsilyl, and carbobenzoxy groups. S-Protecting groups include methyl, tert-butyl, benzyl, and carbobenzoxy groups.

The present invention also provides a process for preparing the above-described oligonucleoside and chimeric oligonucleotide analog compounds using the dimeric nucleoside compounds of this invention, this process comprising joining a 5'-end nucleoside, a middle, bifunctional, unit and a 3'-end nucleoside, by conventional synthetic organic methods known in the art, to produce various oligomers which are useful as antisense compounds.

The present invention further provides an improved process of preparing 3'-O-t-butyldimethylsilyl 2'-deoxynucleosides 6, 25, 31, and 38 in very high yield by treatment of the corresponding 5'-dimethoxytrityl nucleosides with zinc bromide in nitromethane.

This invention also provides a method for the synthesis of the novel bifunctional nucleosides of Formula I, such as 10 and 18, from readily available AZT. These nucleosides are useful as precursors of repeating units in the oligonucleotide analogs of the invention of 3 bases and more having NCC internucleoside linkages.

A further novel aspect of this invention is the synthesis of previously undescribed 5'-carbon funtionalized 2'-deoxynucleosides 26–28, 32–34 and 39–41. These nucleosides are also critical intermediates in the synthesis of NCC linked oligonucleosides. Furthermore, the generally applicable Dess-Martin oxidation (Zon)/Horner-Emmons reaction combination described herein for the synthesis of 39 is an improvement over the Swern/Wittig protocol described for 5'-carbon funtionalization described in the literature.

A general method for the synthesis of oligonucleosides uniformly linked by the NCC internucleoside linkage is described in Scheme 1. Thus, referring to Scheme 1, reductive coupling of bifunctional nucleoside 2 with 7'-aldehyde 3 provides a 7'-functionalized dimer. This dimer, after synthetic elaboration to a 7'-aldehyde can either be coupled to the 5'-end synthon 1 to give a trimer or the chain extension cycle may be continued through repeated couplings with synthon 2 to prepare long chain oligomer analogs 4 uniformly linked by the NCC backbone.

Synthesis of a trinucleoside is illustrated in Scheme 2. Thus the dimer 11 is synthesized from the aldehyde 9 and bifunctional amine-nucleoside 10 and sodium cyanoborohydride under reductive amination conditions. Similarly the dimer aldehyde 13, prepared from the corresponding ester 12, is reductively coupled with amine 14 to give the trimer containing two NCC internucleoside linkages.

Scheme 3 depicts a synthetic pathway for bifunctional nucleosides of Formula I.

Scheme 4 depicts a synthetic pathway for critical intermediates 25–28, 31–34 and 37–40 used for the synthesis of heterotrimers and longer oligomers containing NCC internucleoside linkages; use of these intermediates to synthesize heterodimers having an NCC internucleoside linkage is illustrated.

The preparation of 5'-O-carbethoxy-5'-vinyl-3'-t-butyldimethylsilyl thymidine 45, which is a key intermediate for the synthesis of OCC linked trimers 48 and longer oligomers, is summarized in Scheme 5. Bifunctional nucleoside 45 is synthesized by a Grignard reaction between aldehyde 44 and vinylmagnesium bromide followed by carbethoxylation of the resulting alcohol with ethyl chloroformate and benzoylation.

Reductive alkylation between novel bifunctional amine-nucleoside 52 and formyl-nucleoside 51, as summarized in Scheme 6, can be employed to prepare CNC linked trimers 54 and longer oligomers.

A general scheme for synthesizing CCN linked trimers 60 and longer oligomers is shown in Scheme 7.

A further novel aspect of this invention is the synthesis of N-protected-3'-acetaldehyde-nucleoside 57 via $OSO_4$ hydroxylation of 3'-vinyl-nucleoside 56 and subsequent oxidation of the diol with $NaIO_4$. Similar reductive alkylation of 3'-aldehyde 57 and 5'-amine 58 provides various CCN dimers 59, trimers 60, and longer oligomers. This improved method facilitates preparing oligonucleoside sequence of 3 bases and longer having a three carbon-one nitrogen atom or three carbon-one oxygen replacement of the natural phosphodiester internucleoside linkage. As has been reported in the literature (Uhlmann et al., *Chemical Review*, 9 (4): 544–584; Matteucci, M., *Tetrahedron Letters*, 1990, 2385), oligonucleotide analogs having contiguous stretches of two or more non-phosphodiester internucleoside linkages, such as the oligonucleosides and chimeric oligonucleotide analogs of the present invention, are expected to provide far better nuclease resistance properties than oligonucleotide analogs having isolated (one at a time) non-phosphodiester internucleoside linkages.

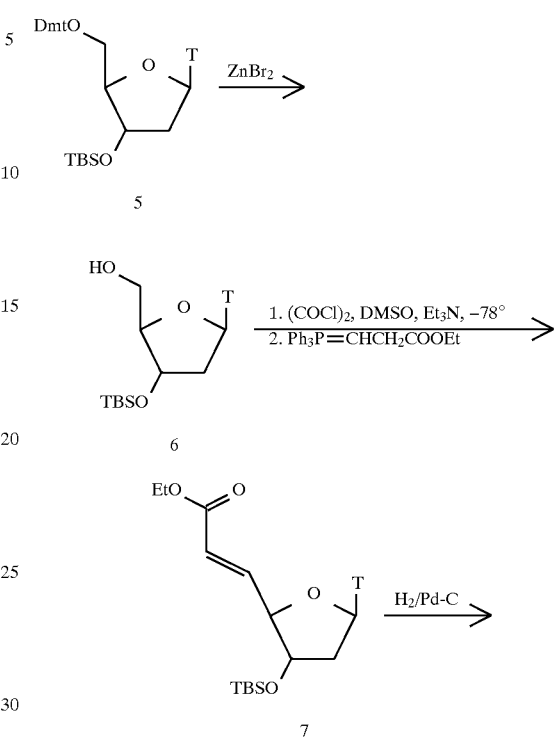

Scheme 2
Synthesis of NCC Linked Trimer [a]

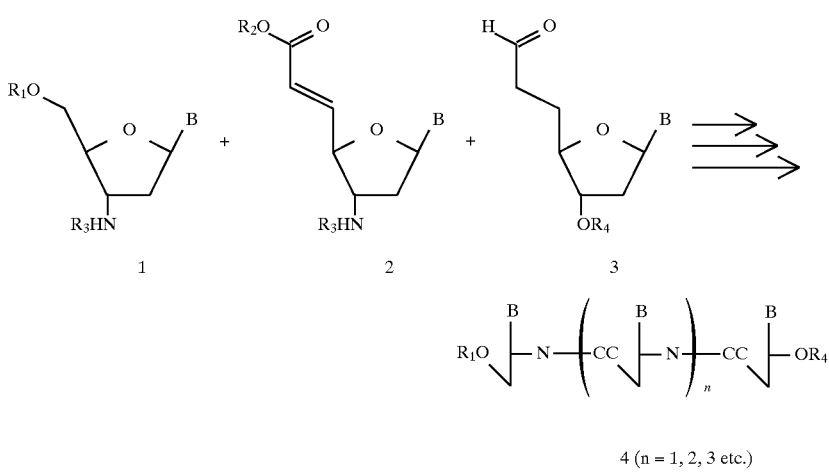

Scheme 1 [a,b,c,d]
General Scheme for synthesis of NCC-linked oligonucleosides

[a] a: B = T, b: B = $A^{Bz}$, c: B = $C^{Bz}$, d: B = $G^{iB}$; Bz=Benzoyl, iB=isoButyryl
[b] $R_1=R_2=R_3=R_4$=H and/or independently alkyl, lower alkenyl, acyl, dimethoxytrityl, t-butyldimethylsilyl, phosphoramidyl etc.
[c] For the synthesis of intermediates 1 and 2, see Scheme 3;
For the synthesis of intermediates 3 see Scheme 4;
For the synthesis of ncc-linked trinucleoside see Scheme 2
[d] Further manipulation such as protection of internucleoside NH group, deprotection of terminal 3'-hydroxyl group followed by phosphoroamidylation, described in Schemes 2 and 4, and obvious to one practiced in the art will prepare the trimers, tetramers, and longer oligomers for incorporation in automated DNA synthesis, if desired.

11
-continued
Scheme 2
Synthesis of NCC Linked Trimer [a]
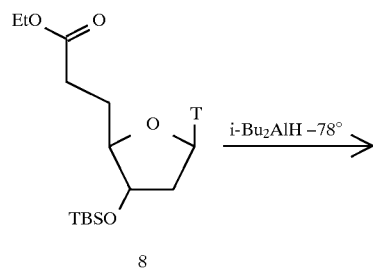
8
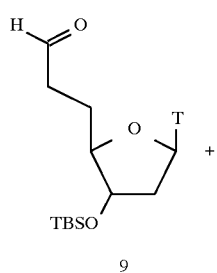
9
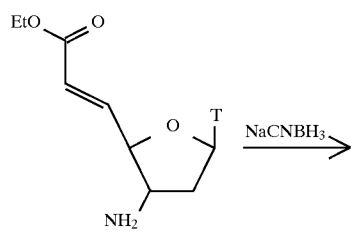
10 (Scheme 3)
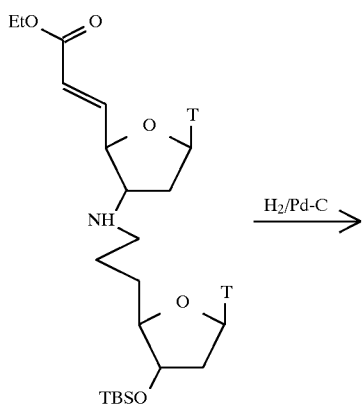
11
12
-continued
Scheme 2
Synthesis of NCC Linked Trimer [a]
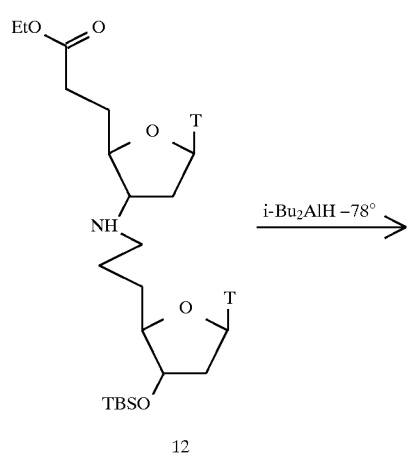
12
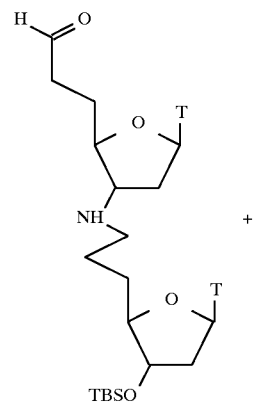
13
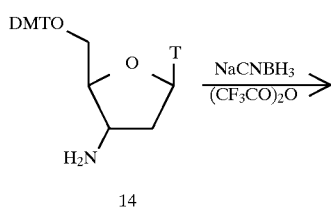
14

Scheme 2
Synthesis of NCC Linked Trimer [a]
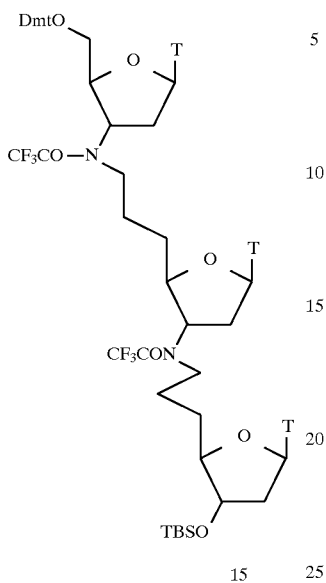
[a] Dmt = dimethoxytrityl, TBS = t-butyldimethylsilyl
Scheme 4
Critical Intermediates for Synthesis of Heterotrimers, Tetramers, etc.
A. AnccT
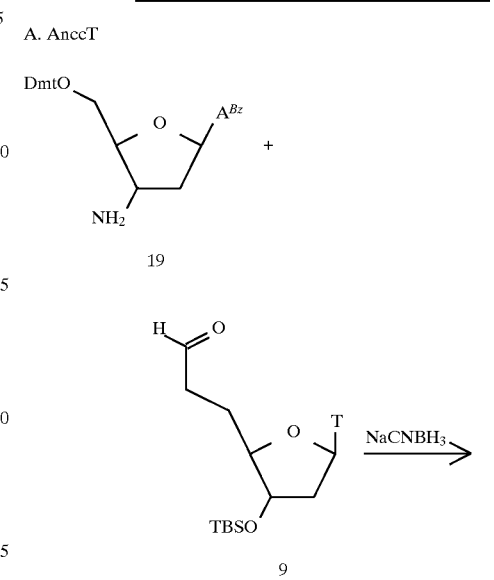
Scheme 3
Synthesis of bifunctional nucleosides
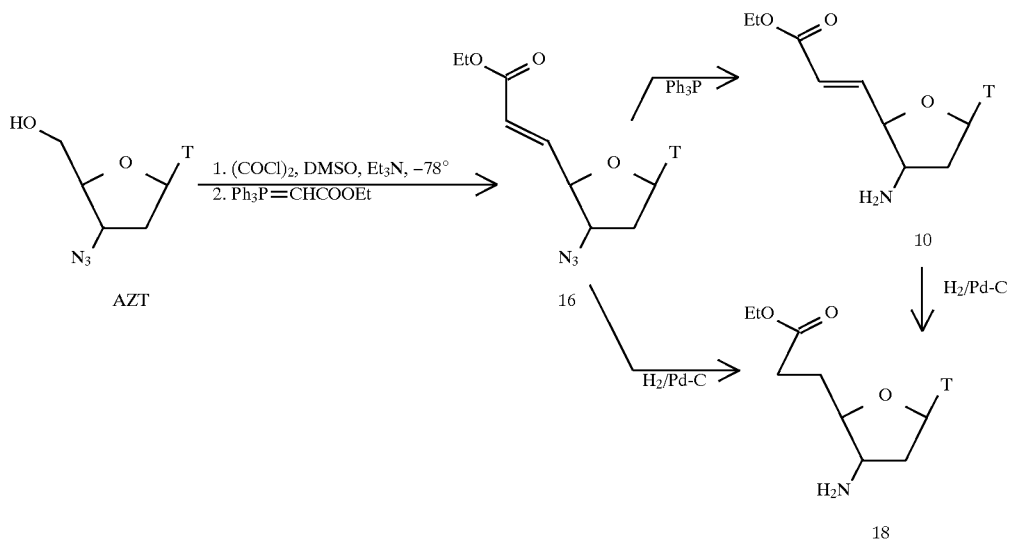

5,892,024
-continued
Scheme 4
Critical Intermediates for
Synthesis of Heterotrimers, Tetramers, etc.
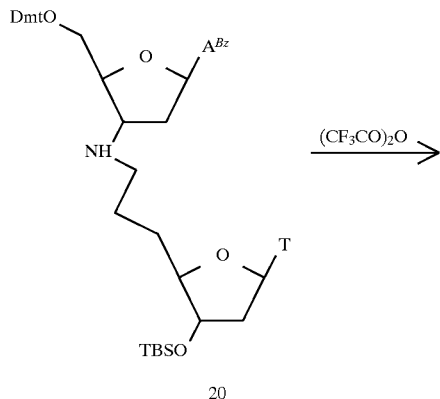
20
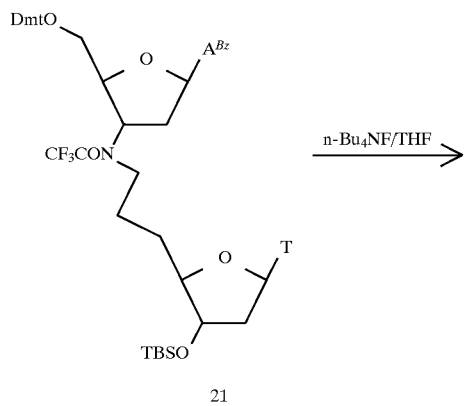
21
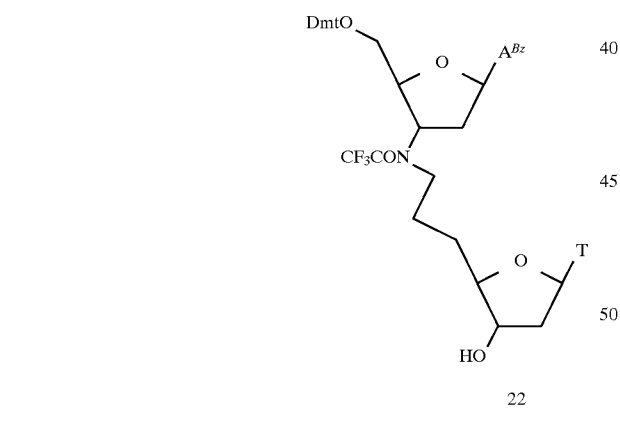
22
B. TnccA
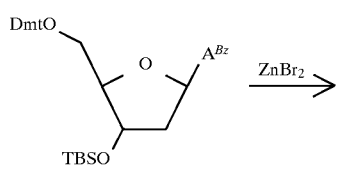
24
-continued
Scheme 4
Critical Intermediates for
Synthesis of Heterotrimers, Tetramers, etc.
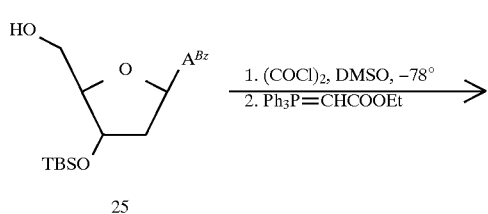
25
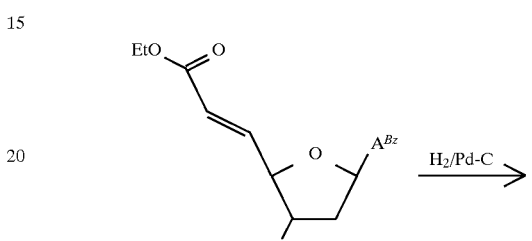
26
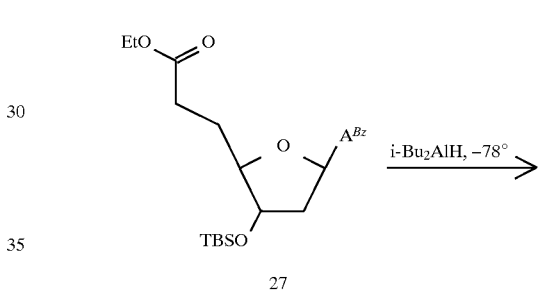
27
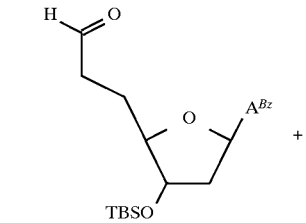
28
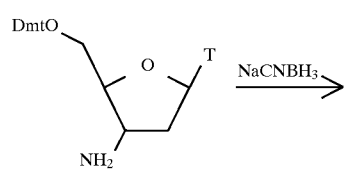
14

-continued
Scheme 4
Critical Intermediates for
Synthesis of Heterotrimers, Tetramers, etc.
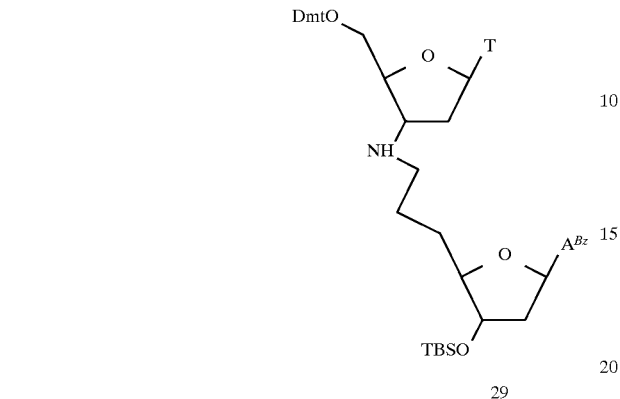
29
C. TnccC
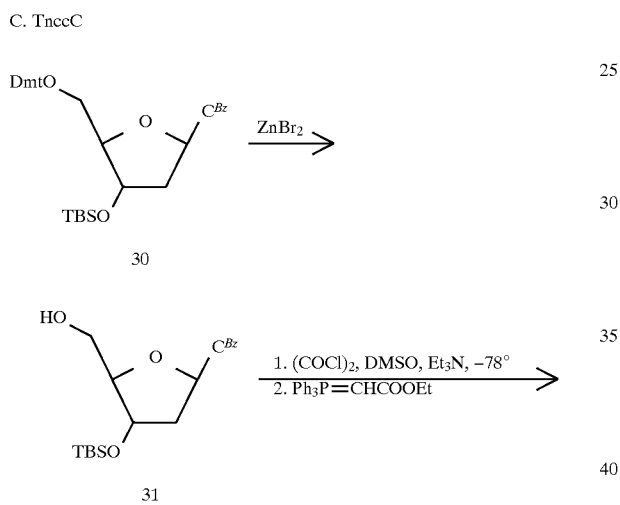
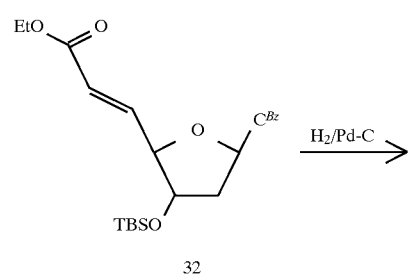
32
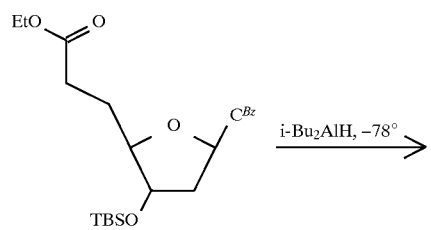
33
-continued
Scheme 4
Critical Intermediates for
Synthesis of Heterotrimers, Tetramers, etc.
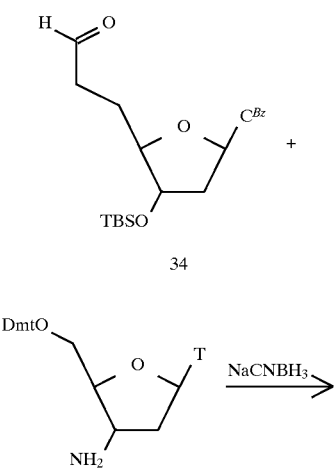
D. TnccG
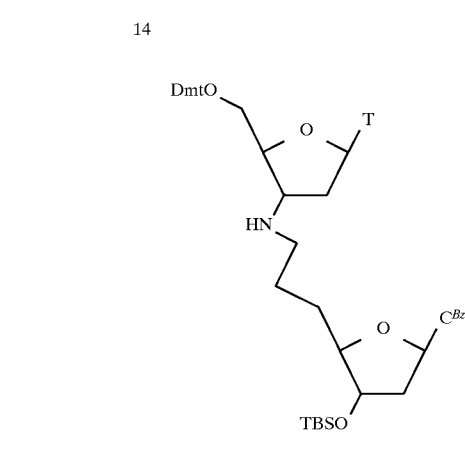

Scheme 4
Critical Intermediates for
Synthesis of Heterotrimers, Tetramers, etc.
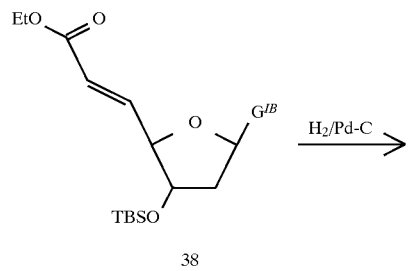
38
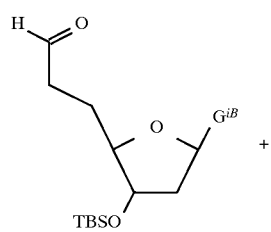
39
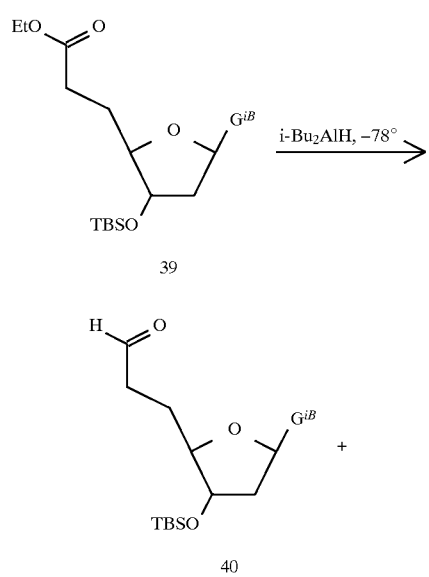
40
Scheme 4
Critical Intermediates for
Synthesis of Heterotrimers, Tetramers, etc.
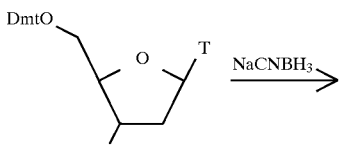
14
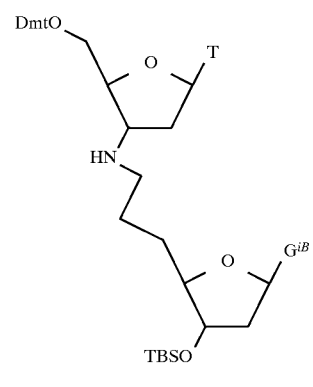
41
Scheme 5
General Scheme for Synthesis of OCC Linked Trimers, Tetramers and Longer oligomers
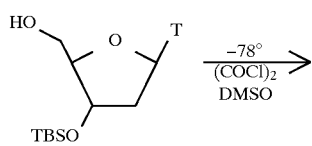
43
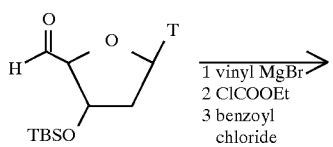
44

-continued
Scheme 5
General Scheme for Synthesis of OCC Linked Trimers, Tetramers and Longer oligomers
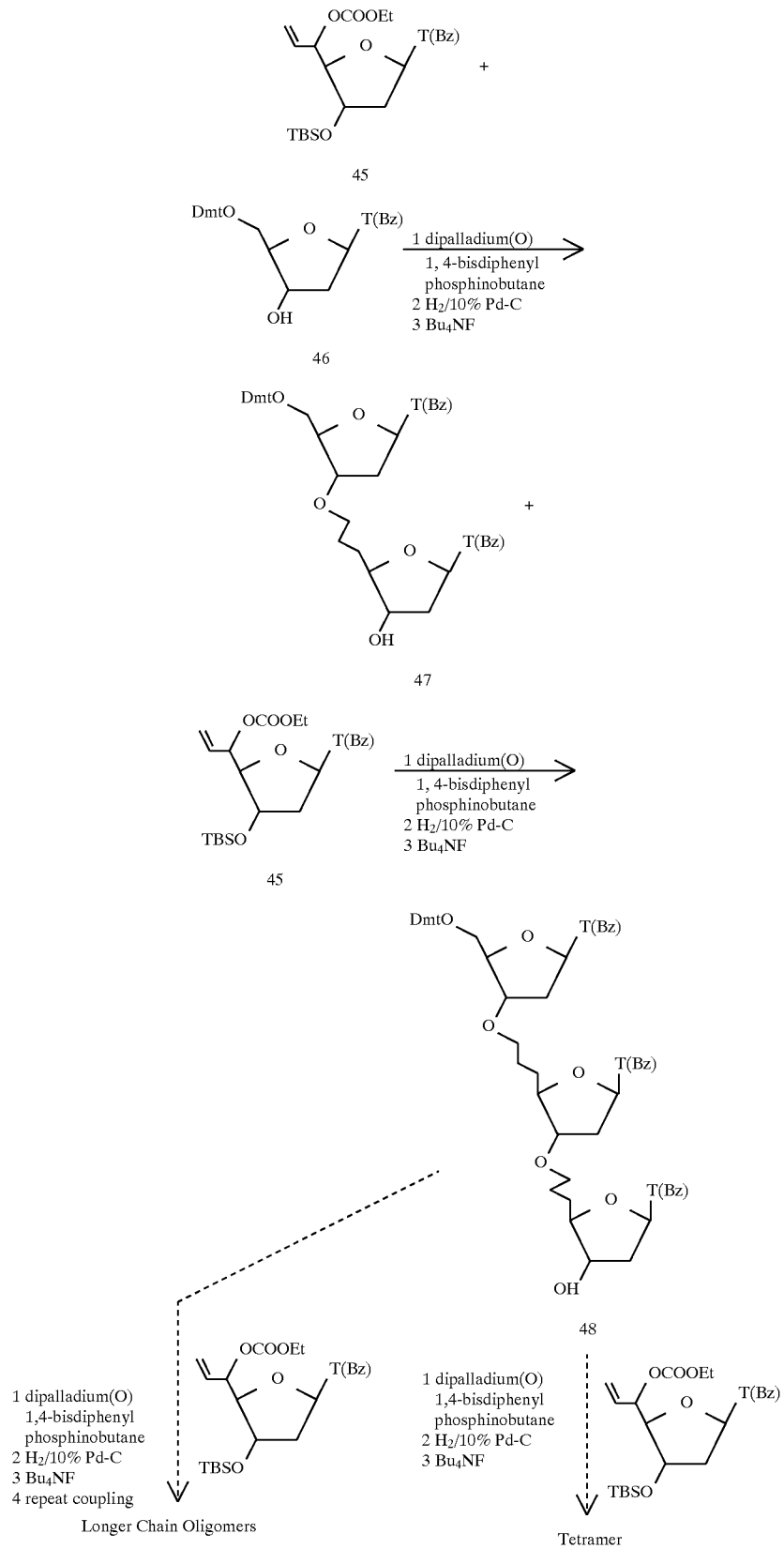

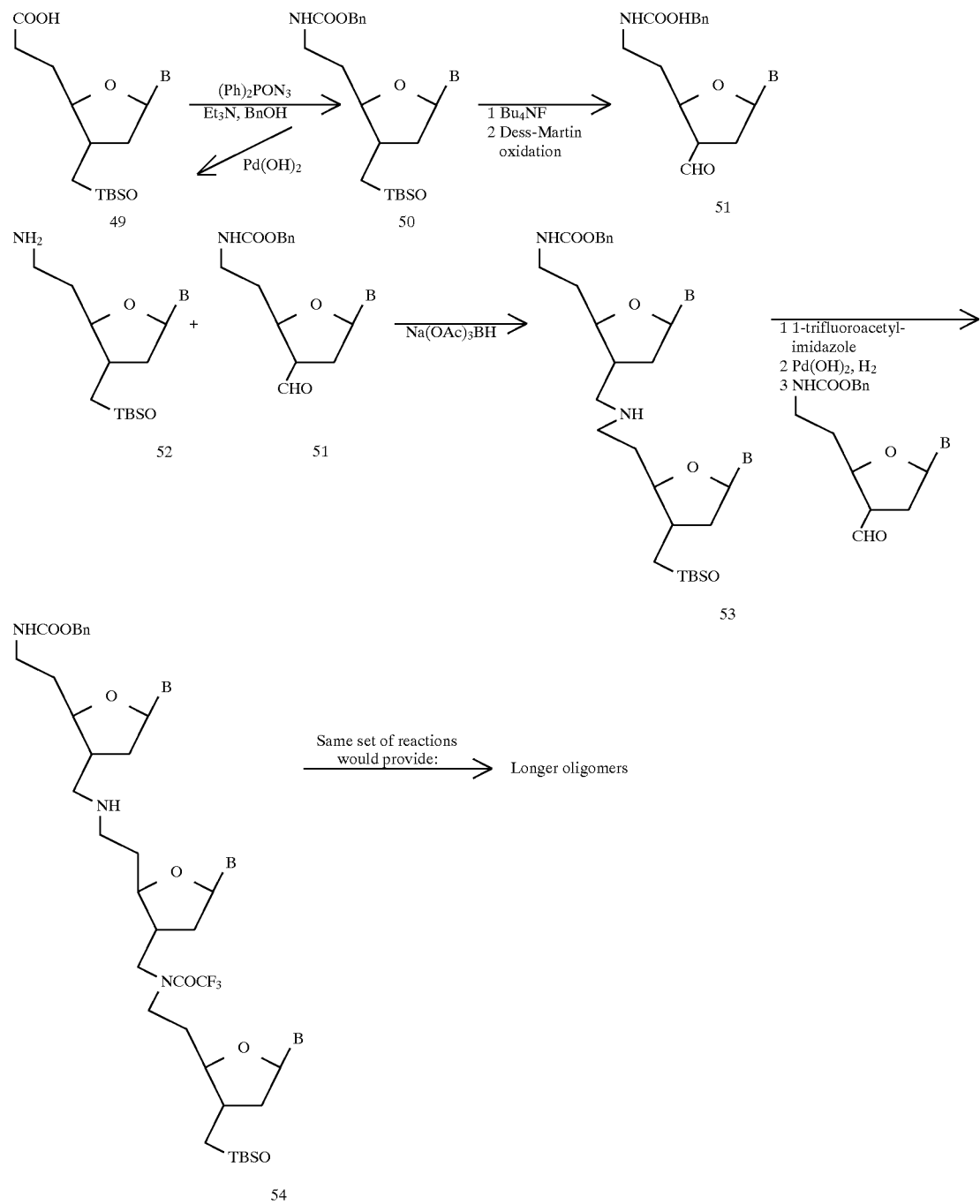
Scheme 6
General Scheme for Synthesis of CNC Linked Trimers, Tetramers and Longer oligomers

Scheme 7
General Scheme for Synthesis of CCN Linked Trimers, Tetramers and Longer oligomers

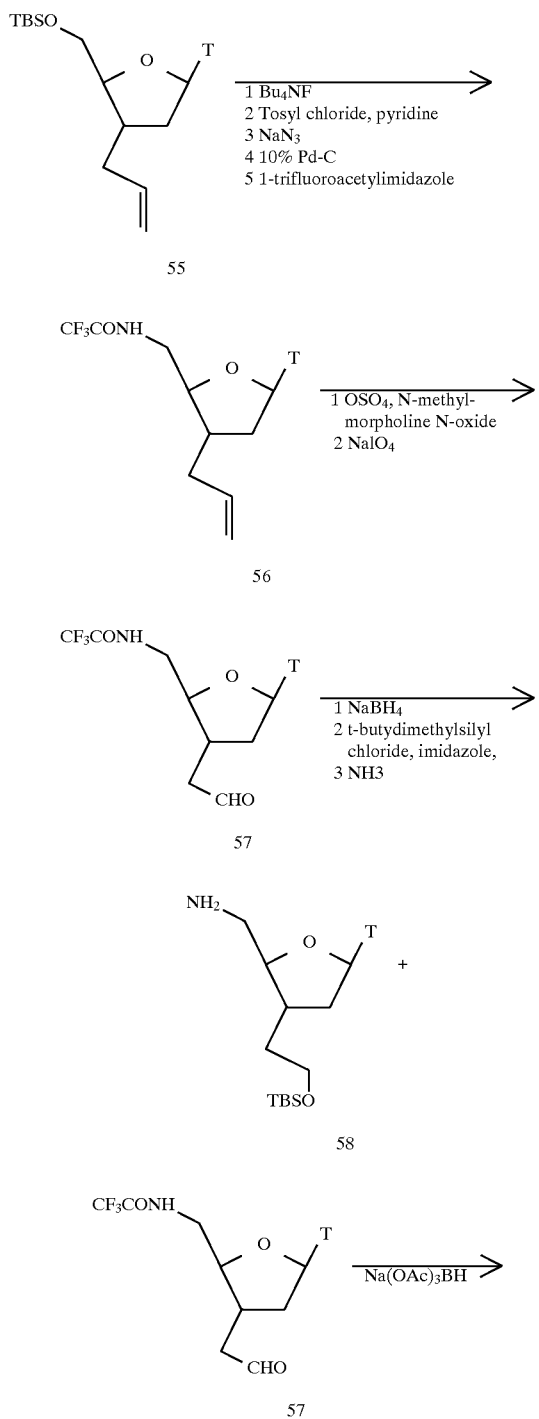

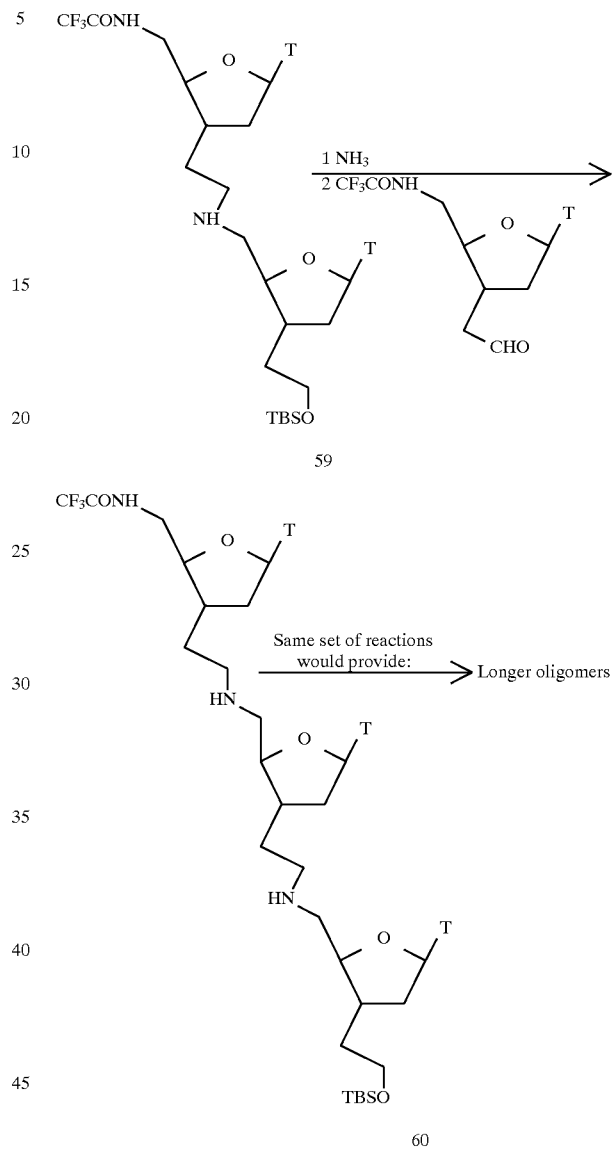

This invention also contemplates pharmaceutically acceptable salts of the compounds of Formula I. It is well known in the pharmacological arts that nontoxic addition salts of pharmacologically active amine compounds do not differ in activities from their free base.

Pharmaceutically acceptable salts include both acid and base addition salts. "Pharmaceutically acceptable salt" refers to those salts which retain the biological effectiveness and properties of the free bases and which are not biologically or otherwise undesirable. Suitable pharmaceutically acceptable acid addition salts can be formed with inorganic acids such as hydrochloric acid, hydrobromic acid, sulfuric acid, nitric acid, phosphoric acid, and the like, and organic acids such as acetic acid, propionic acid, glycolic acid, pyruvic acid, fumaric acid, tartaric acid, citric acid, benzoic acid, cinnamic acid, mandelic acid, methanesulfonic acid, and p-toluenesulfonic acid, and the like.

Pharmaceutically acceptable base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic non-toxic bases include salts of primary, secondary, and tertiary amines, substituted amines, including naturally occurring substituted amines, cyclic amines and basic ion iexchange resins, such as isopropylamine, tripropylamine, ethanolamine, 2-diethylaminoethanol, 2-dimethylaminoethanol, dicyclohexylamine, lysine, arginine, histidine, caffeine, procain, hydrabamine, choline, betaine, ethylenediamine, glucosamine, methylglucamine, theobromine, purines, peperizines, piperidine, polyamine resins and the like. Particularly preferred organic non-toxic bases are isopropylamine, diethylamine, ethanol-amine and dicyclohexylamine.

In one embodiment, the compounds of the present invention comprise oligomeric antisense agents, as shown in Formula II, of about 6 to about 60 bases, preferably from about 9 to about 50 bases, more preferably from about 12 to about 25 bases, most preferably from 15 to 18 bases. These antisense agents can be formulated into compositions together with one or more non-toxic physiologically acceptable carriers, adjuvants or vehicles which are collectively referred to herein as carriers, for parenteral injection or oral administration, in solid or liquid form, for rectal or topical administration, or the like.

The compositions can be administered to humans and animals either orally, rectally, parenterally (intravenous, intramuscularly or subcutaneously), intracisternally, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants. These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents that delay absorption, for example, aluminum monostearate and gelatin.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as, for example, quaternary ammonium compounds, (g) wetting agents, as for example, cetyl alcohol and glycerol monostearate, (h) adsorbents, as, for example, kaolin and bentonite, and (i) lubricants, as, for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules, using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, particularly cottonseed oil, ground-nut oil, corn germ oil, olive oil, castor oil and sesame oil, glycerol, tetrahydrofurfuryl alcohol, polyethyleneglycols and fatty acid esters of sorbitan or mixtures of these substances, and the like. Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal or vaginal administration are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and, therefore, melt in the rectum or vaginal cavity and release the active component.

Dosage forms for topical administration include ointments, powders, sprays and inhalants. The active component is admixed under sterile conditions with a physiologically acceptable carrier and any preservatives, buffers or propellants as may be required. Ophthalmic formulations, eye ointments, powders and solutions are also contemplated.

Actual dosage levels of the active ingredient in the compositions may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

The total daily dose of the active ingredients administered to a host in single or divided doses may be in amounts, for example, of from about 0.5 mg to about 10 mg per kilogram of body weight. Dosage unit compositions may contain such amounts or such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

The present invention is further directed to a method of inhibiting the expression of a gene that comprises administering to a host mammal in need of such inhibition an inhibition-effective amount of a compound of Formula II, in which that compound hybridizes to a nucleotide sequence of the gene.whose expression is to be inhibited. In a preferred embodiment, the compound of Formula II is dissolved or dispersed in a physiologically tolerable carrier.

As discussed elsewhere herein, inhibition of the expression of a gene can be effected by interfering with transcription, translation, or RNA processing. Hence, the activity of an antisense molecule can be at the level of messenger RNA or genomic DNA. So, for example, when an antisense molecule hybridizes to messenger RNA, translation is inhibited. When an antisense molecule hybridizes to genomic DNA, transcription is inhibited. An antisense molecule may also bind to other nucleic acid species in a cell, including heterogeneous nuclear RNA (hnRNA) and pre-messenger RNA.

A host mammal in need of the inhibition of the expression of a gene suffers from a disease state in which the expression of the gene is implicated. Such disease states include a variety of cancers, in which the expression of an oncogene or oncogenes is implicated, cystic fibrosis, Huntington's chorea, and other such disease states in which the aberrant expression of a normal gene or the expression of an abnormal gene is responsible, in whole or in part, for the disease condition.

As used herein, an "inhibition-effective amount" is the amount of a compound of the present invention which is sufficient to inhibit the expression of the gene whose expression is to be inhibited. Means for determining an inhibition-effective amount will depend, as is well known in the art, on the nature of the gene to be inhibited, the type of inhibition desired (i.e., inhibition of translation or transcription or both), the mass of the subject being treated, and the like.

It is to be understood that the compound of the Formula II used in the inhibition of the expression of a gene must hybridize to a sequence of that gene in such a way as the expression of that gene is inhibited. That is, the nucleotide bases used to make a compound of the Formula II (B in Formula II as defined above) must hybridize to the nucleotide sequence of the gene whose expression is to be inhibited. Such sequence can readily be ascertained from the known sequence of that gene, and the appropriate antisense molecule of Formula II can therefore be prepared. Hybridization of greater than about 90 percent homology (identity), and more preferably about 99 percent homology, is contemplated in the present invention.

The following examples further illustrate the invention and are not to be construed as limiting of the specification and claims in any way.

EXAMPLES

Example 1

Preparation of 3'-O-t-butyldimethylsilyl thymidine (6)

A stock solution of zinc bromide was prepared by dissolving zinc bromide (21 g) in nitromethane (150 ml) and water (1.5 ml). The zinc bromide solution (93.75 mM; 5 eq.) was added to a stirred solution of 5'-O-dimethoxytrityl-3'-O-t-butyldimethylsilyl thymidine (12.34 g; 18.75 mM ) in nitromethane (150 ml) at room temperature. Thin layer chromatography (TLC) examination after 20 minutes showed complete disappearance of all starting materials. The reaction mixture was poured into 1M. aqueous ammonium acetate solution (450 ml) and extracted into ethyl acetate (200 ml×2). The organic layers were combined and washed with brine (200 ml) and dried over anhydrous sodium sulfate. The crude product was purified by flash chromatography ($SiO_2$:60% EtOAC/Hex) to give 6.33 g (95%) of the pure title compound.

Example 2

5'-Carbethoxymethylene-3'-aminoethyl-5',3'-dideoxythymidinyl [3'(O)—>5'(C)]-3'"tert-butyldimethylsilyl-5"-deoxythymidine (11)

Sodium cyanoborohydride (1M in THF; 4.25 mM; 4.25 ml) was added via a syringe pump over 2 hours to a solution of amine 10 (500 mg;1.77 mM) and 7'-aldehyde (9; 812 mg) in ethanol (18 ml) and phosphate buffer (pH 5.5; 3.5 ml ) at 0° C. After 3 hours of additional stirring at 0' C., TLC examination indicated completion of the reaction. The reaction mixture was diluted with chloroform (25 ml) and washed with water (5 ml) and brine (5 ml) and dried over anhydrous sodium sulfate. The crude product was purified by flash chromatography ($SiO_2$: 100 g; 5% saturated. $NH_3$ in MeOH in EtOAc). The yield (500 mg) of reaction product was 50%. $R_f$–0.33(10% saturated $NH_3$ in MeOH in EtOAc). FABMS: MH+=676.
$^1$H NMR ($CDC_3$): 7.08 (s,1H), 6.97 (s,1H), 6.93 (dd, 1H, J=15 Hz, 5 Hz), 6.18(t, 1H, J=6 Hz), 6.04 (dd, 1H, J=5 Hz,3 Hz), 6.0 (t, 1H, J=6 Hz), 4.14 (q. 1HJ=7 Hz), 3.97 (m, 1H), 3.68 (m,1H), 3.18 (m, 1H), 2.61 (m,1H), 2.16 (m, 4H), 1.7–1.6 (m, 1H), 1.81 (S, 6H), 1.25 (t, 3H, J=7 Hz), 0.78 (S, 9H), –0.1 (S, 6H) ppm.

Example 3

5'-Carbethoxymethyl-3'-aminoethyl-5', 3'dideoxythymidinyl [3'(O)—>5'(C)]-3"-tert-butyldimethylsilyl-5"-deoxythymidine (12)

A solution of unsaturated dimer (11; 450 mg) in methanol was stirred under 1 atmosphere of hydrogen in the presence of 10% Pd/C (90 mg; 20 wt %) for 18 hours. The catalyst was then filtered through celite and filtrate was evaporated to give 450 mg of the desired ester 12.
$R_f$32 0.33 (10% saturated. $NH_3$ in MeOH in EtOAc). FABMS: MH+=678. $^1$HNMR ($CDCl_3$): 7.03 (s, 1H), 6.99 (s,1H), 6.02 (t, 2H), 4.01 (q, 2H, J=7 Hz), 3.97 (m, 1H), 3.63 (m, 2H), 2.54 (m, 1H), 2.33 (m, 2H), 2.08–1.8 (m, 10H), 1.81 (s,6H), 1.51 (m, 2H), 1.25 (t, 3H, J=7 Hz), 0.78 (S, 9H), –0.1 (S, 6H) ppm.

Example 4

5'-Formylmethyl-3'-aminoethyl-5',
3'dideoxythymidinyl [3'(O)—>5'(C)]-3"-tert-
butyldimethylsilyl-5"-deoxythymidine (13)

Diisobutylaluminum hydride (1M in hexane; 1,8 mM; 1.8 ml) was added slowly via syringe to a solution of dimer (12; 200 mg; 0.3 mM) in dry THF (3ml) at −78° C. TLC examination after 3 hours at −78° C. showed disappearance of all starting material, and the reaction was quenched by the addition of methanol (193 µl) at −78° C. The reaction mixture was then warmed to 0° C. and aqueous sodium sulfate (350 µl) was added, followed by ether (5.2 ml) and sodium sulfate. The mixture was vigorously stirred at room temperature for 20 minutes and then filtered through a Buchner funnel. The filtrate was evaporated to give 155 mg of the crude aldehyde 13. $^1$HNMR examination of this crude product clearly showed the aldehyde proton at 9.64 ppm. This aldehyde was used in the next step without further purification (Yield=50%).

Example 5

5'-Dimethoxytritylmethyl-3'-aminoethyl-5',
3'dideoxythymidinyl [3'(O)—>5'(C)]-3'-aminoethyl-
5',3"-dideoxythymidyl [3'(O)—>5'(C)]-3'-tert-
butyldimethylsilyl-5"-deoxythymidine Sodium cyanoborohydride (1M in THF; 0.3 mM; 0.3ml) was added slowly via syringe to a solution of crude aldehyde (13; 155 mg;

approx. 0.15 mM) and 3'-amino-3'-deoxy-5'-dimethoxytrityl thymidine (14; 0.14 mM; 75 mg) in ethanol (1.5 ml) and phosphate buffer (pH 5.5, 0.3 ml) at 0° C. After three additional hours of stirring at 0° C., TLC examination indicated completion of the reaction. The reaction mixture was diluted with ethyl acetate (15 ml) and washed with water (4 ml) and brine (2 ml) and dried over anhydrous sodium sulfate. The crude product was purified by flash chromatography (SiO$_2$: 5 g, 5% saturated. NH$_3$ in MeOH in EtOAc). The yield of title compound (trimer) was 50% (81 mg). R$_f$-0.15 (5% saturated. NH$_3$ in MeOH in EtOAc).
$^1$HNMR (CDCl$_3$): 7.62 (s, 1H), 7.44–7.28 (m, 9H), 7.18 (s, 1H), 7.10 (s, 1H), 6.30 (t, 1H, J=6 Hz), 6.13 (t, 1H, J=6 Hz), 6.05 (t, 1H, J=6 Hz), 4.11 (m, 1H), 3.92 (m, 1H), 3.84 (m, 1H), 3.80 (s,6H), 3.75 (m, 1H), 3.55–3.4 (m, 2H), 2.65–2.2 (m, 14H), 1,92 (s,3H), 1.90 (s, 3H), 1.68 (m, 4H), 1.52 (s, 3H), 0.85 (s, 9H), 0.05 (s, 6H) ppm.

Example 6

5'-Dimethoxytrityl-3'-(N-trifluoroacetyl)aminoethyl-
5',3'dideoxythymidinyl [3'(O)—>5'(C)]-3'-(N-
trifluoroacetyl)aminoethyl-5',3'-dideoxythymidyl[3'
(O)—>5'(C)]-3'-tert-butyldimethylsilyl-5"-
deoxythymidine (15)

Trifluoroacetic anhydride (0.6 mM; 84.75 µl) was added dropwise via syringe to a solution of the trimer of Example 5 (70 mg; 0.06 mM) and triethylamine (1.2 mM; 167 µl) in methylene chloride (1 ml) at 0° C. TLC examination after 30 minutes showed complete disappearance of all starting material. The reaction mixture was evaporated to dryness and the residue was purified by short column chromatography to afford the title compound. R$_f$: 0.55 (5% saturated NH$_3$ in MeOH in Et.OAc). FABMS: MH+=1353: (M–H)−=1351.
$^1$HNMR(CDCl$_3$): 7.55 (s, 1H; 5'-thymine 5-H); 7.10 (s, 1H, thymine 5-H), 7.02 (s, 1H, thymine 5-H), 6.38 (t, 1H, J=6 Hz; 5'-ribose 1'-H),6.10 (t, 1H, J=6 Hz; ribose 1'-H), 5.95 (t, 1H, J=6 Hz; ribose 1'-H), 1.96 (s, 3H, thymine 5-Me), 1.90 (s, 3H, thymine 5-Me), 1.6 (s, 3H, 5'-thymine-5-Me), 0.85 (s, (H, t-BuSi), 0.05 (S, 6H, Si-Me$_2$).

Example 7

5'-Carbethoxymethylene-3'-azido-5',
3'dideoxythymidine (16)

A solution of DMSO(426 µl, 6 mM) in methylene chloride (1.5 ml) was added to a stirred solution of oxalyl chloride (288 µl, 3.3 mM) in methylene chloride (7.6 ml) at −78° C. under nitrogen. After 5 minutes, a solution of 3'-azido-3'-deoxythymidine (801 mg; 3 mM) in DMSO/CH$_2$Cl$_2$ (1.12 ml/3.47 ml) was added over a ten minute period. Stirring was continued for 20 minutes, and then triethylamine (2.09 ml, 15 mM) was added and the reaction mixture was stirred for an additional 5 minutes. (Carbethoxymethylene) triphenylphosphorane (1.57 g; 4.5 mM) was added in a solution of methylene chloride (9 ml), and the reaction mixture was stirred at −78° C. for 30 minutes and then allowed to stand at room temperature for 1 hour. The crude reaction mixture was then quenched with cold water (20 ml) and extracted into ethyl acetate (2×50 ml), washed with brine and dried over anhydrous sodium sulfate. The crude product was purified by flash chromatography (SiO$_2$: 60 g; 60% ethyl acetate/hexane) to afford 765 mg (76%) of the title compound. R$_f$–0.47(7/3 EtOAc/Hexane).
IR: 2107 cm−(N$_3$): FAB-MS: MH+=336;
$^1$HNMR (CDCl$_3$): 7.04 (s, 1H), 6.94 (dd, 1H, J=5.5 Hz, 1.8 Hz), 6.16–6.10 (m, 2H), 4.34 (t, 1H J=6 Hz), 4.20 (q, 2H, J=7 Hz), 4.09 (m, 1H), 2.4 (m,2H), 1.91 (s, 3H), 1.28 (t, 3H, J=7 Hz).

Example 8

5'-Carbethoxymethyl-3'-amino-5',3'-
dideoxythymidine (18)

A solution of the ester of Example 7 (16; 700 mg, 2.09 mM) in methanol (15 ml) was subjected to hydrogenation in a Parr apparatus (30 psi) in the presence of 10% Pd/C (210 mg; 30 wt %). The hydrogenation reaction was completed after 24 hours. The catalyst was filtered and the filtrate evaporated to give 620 mg (96%) of the title compound. R$_f$=0.3(5% saturated. NH$_3$ in MeOH in EtOAc). FAB-MS: MH+=312.
$^1$HNMR(CDCl$_3$: 7.4(s,1H), 6.11 (dd, 1H, J=5 Hz, 3 Hz), 4.1 (q,2H, J=7 Hz), 3.62 (m, 1H), 2.51–2.10 (m, 7H), 1.87 (s, 3H), 1.24 (t, 3H, J=7 Hz) ppm.

EXAMPLE 9

5'-Carbethoxymethylene-3'-amino-5',3'-
dideoxythymidine (10)

Triphenylphosphine (786 mg; 3 mM) was added to a stirred solution of the ester of Example 7 (16; 700 mg: 2.09 mM) in THF/H$_2$O (10 ml/1 ml) and the reaction was monitored by gas evolution via an attached gas bubbler. The reaction was completed after 3 hours. The mixture was evaporated in vacuo and the crude oil was chromatographed over SiO$_2$ (50 g), eluting with 5% saturated. ammonia in methanol/ethyl acetate to afford a 93% yield (600 mg) of the title compound. R$_f$=0.3 (5% saturated. NH$_3$/MeOH in EtOAc). FAB-MS: MH+=310.
$^1$HNMR(CDCl$_3$): 7.17 (s,1H), 6.84 (dd, 1H, J=15.5 Hz, 5.5 Hz),5.96 (dd, 1H, J=5 Hz, 3 Hz), 5.72 (dd, 1H, J=15.5 Hz, 1.5 Hz), 3.95 (q, 2H, J=7 Hz), 3.2 (m, 1H),2.2–1.9 (m,3H), 1.67 (S, 3H), 1.04 (t, 3H, J=7 Hz) ppm.

Example 10

5'-O-dimethoxytrityl N-benzoyl-thymidine

5'-O-Dimethoxytrityl-3'-O-t-butyldimethylsilyl thymidine (5 g) was dissolved in dry pyridine (50 ml) and then benzoyl chloride (1.5 eq.) and diisopropy-ethyl amine (1.5 eq.) were added to the solution. The resulting mixture was stirred overnight at room temperature. The solvent was evaporated, and the residue was diluted with ethyl acetate, washed with water followed by brine and purified by flash chromatography using 30% ethyl acetate/hexane. The benzoylated product (2.0 g) was dissolved in THF (25 ml) and cooled to −78° C. and then added to 1.0M Bu$_4$NF solution in THF (1.5 eq.). After 2 hours, the .reaction mixture was diluted with ethyl acetate, washed with water followed by brine, and dried over sodium sulfate. The title compound was purified by flash chromatography using 70% ethyl acetate/hexane.

Example 11

5'-Vinyl-3'-O-t-butyldimethylsilyl thymidine

3'-O-t-Butyldimethylsilyl thymidine 4'-aldehyde (5.0 g; azeotroped twice with toluene, 25 ml) was dissolved in dry THF (60 ml) and cooled to −78° C., followed by addition of 1.0M solution of vinylmagnesium bromide (2.5 eq.) in THF. The reaction mixture was stirred for 30 minutes and then quenched with saturated aqueous NH$_4$Cl, diluted with ethyl acetate, washed with water (2×100 ml) and then with brine. Then the organic layer was dried. The title compound was purified by flash chromatography using 30% ethyl acetate/hexane, affording a 43% yield of the desired alcohol.

Example 12: 5'-O-Carbethoxy-5'-vinyl-3'-O-t-butyldimethylsilyl thymidine

To a solution of 5'-vinyl-3'-O-t-butyldimethylsilyl thymidine (2.0 g) in 30 ml of methylene chloride was added ethyl chloroformate (6 eq.) and pyridine (12 eq.) and the resulting mixture was stirred for 2 hours. The mixture was diluted with ethyl acetate, washed with aqueous sodium bicarbonate, then with water (2×25 ml), and then with brine. Then the organic layer was dried. The title compound was purified by flash chromatography using 20% ethyl acetate/hexane.

Example 13

5'-O-Carbethoxy-5'-vinyl-3'-O-t-butyldimethylsilyl N-benzoyl-thymidine

To a solution of 5'-O-carbethoxy-5'-vinyl-3'-O-t-butyldimethylsilyl thymidine (1.7 g) in 20 ml of pyridine was added benzoyl chloride (2.5 eq.) and diisopropyl-ethylamine (95.0 eq.) and the resulting mixture was stirred for 15 hours. The reaction mixture was diluted with ethyl acetate, washed with aqueous sodium bicarbonate followed by brine, and the organic layer was then dried over sodium sulfate. The title compound was purified by flash chromatography using 20% ethyl acetate/hexane.

Example 14

5'-Dimethoxytritylmethyl-3'-O-ethyl-N-benzoyl-thymidinyl [3'(O)—>5'(C)]-5'-deoxy-N-benzoyl-thymidine To a solution of tris(dibenzylidene acetone)dipalladium (O) (75 mg) in 4 ml of dry THF under nitrogen was added 1,4-bisdiphenylphosphinobutane (144 mg), and the resulting mixture was stirred for 15 minutes. The mixture was then heated to 50° C. for 5 minutes and then brought back to room temperature. 5'-O-Dimethoxy-trityl N-benzoyl-thymidine (580 mg) was added to the above mixture and stirred for 10 minutes while heating to 50° C. To the above reaction mixture was added dropwise 1.0 g of 5'-O-carbethoxy-5'-vinyl-3'-O-t-butyldimethylsilyl N-benzoyl-thymidine in 6 ml of THF over a 1 hour period. The crude product was purified by flash chromatography using 25–35% ethyl acetate/hexane to give the dimer in 58% yield. The resulting unsaturated dimer was dissolved in 50 ml of ethyl acetate under nitrogen, and 70 mg of 10% Pd/C was added and the resulting mixture was stirred under an atmosphere of hydrogen for 2 hours. The catalyst was filtered using a celite pad, and the solvent was removed in vacuo to afford 400 mg of the reduced dimer. The silylated reduced dimer was dissolved in 20 ml of THF, cooled to −78° C. and then Bu$_4$NF (1.5 eq.) was added, and the resulting reaction mixture was stirred for 1 hour, diluted with ethyl acetate, washed with water followed by brine, and the organic layer was then dried. The title dimer compound was purified by flash chromatography using 3% methanol/methylene chloride.

Example 15

5'-Dimethoxytrityl-3'-O-ethyl-N-benzoyl-thymidinyl [3'(O)—>5'(C)]-5'-deoxy-3'-O-ethyl-N-benzoyl-thymidyl[3'(O)—>5'(C)]-3'-tert-butyldimethylsilvl-5"-deoxythymidine To a solution of tris(dibenzylidene acetone)dipalladium (O) (4 mol %) and 1,4-bisdiphenylphosphinobutane (12 mol %) was added 80 mg of 5'-dimethoxy-trityl-3'-O-ethyl-N-benzoyl-thymidinyl [3'(O)—>5'(C)]-5'-deoxy-N-benzoyl-thymidine and the mixture was heated to 50° C. To the above reaction mixture was added dropwise 5'-O-carbethoxy-5'-vinyl-3'-O-t-butyldimethylsilyl N-benzoyl-thymidine (2 eq.) in 1 ml of THF over a 30 minute period. The crude trimer was purified by preparative thin layer chromatography using 60% ethyl acetate/hexane. The product was extracted with ethyl acetate and the solvent was removed in vacuo. The trimer was dissolved in 10 ml of ethyl acetate under nitrogen. Then 10 mg of 10% Pd/C was added and the resulting mixture was stirred under an atmosphere of hydrogen. The catalyst was filtered over a celite pad. $^1$H NMR analysis of the trimer confirmed the formation of the desired title compound.

Example 16

5'-Vinyl-5'-deoxy-3'-t-butyldimethylsilyl deoxythymidine

To a solution of methyltriphenyl phosphonium bromide (0.7 mmol) in dry THF at 0° C. was added a solution of sodium bis(trimethylsilylamide) (0.6 mmol) dropwise. After 30 minutes, a solution of 3'-O-t-butyldimethylsilyl thymidine 4'-aldehyde in THF was added dropwise under nitrogen. The reaction mixture was stirred for 2 hours, diluted with ethyl acetate, washed with water, then with brine; and the organic layer was dried over sodium sulfate. The solvent was removed in vacuo and the title compound was purified by flash chromatography using 20% ethyl acetate/hexane, affording a 55% yield of the title compound.

Example 17

3'-O-t-Butyldimethylsilyl-5'-deoxy-5'-hydroxymethyl thymidine

To a solution of 2M 2-methyl-2-butene (1.5 ml, 3 mmol) in 3 ml of anhydrous THF at 0° C., 1.6 eq. of a 1M borane-tetrahydrofuran complex (3 ml, 2 mmol) were added slowly under nitrogen. The solution was stirred for 10 minutes followed by the addition of 5'-vinyl-5'-deoxy-3'-t-butyldimethylsilyl thymidine (0.7 g, 1.9 mmol) in 5 ml of anhydrous THF. The reaction mixture was stirred for 45 minutes, and then placed in the refrigerator for 2 days. Workup was done using an aqueous solution comprising 3.1 eq. of 2M sodium hydroxide and 3.1 eq. of 30% hydrogen peroxide. The solution was added slowly through an addition funnel to the reaction mixture at 0° C., stirred for 1 hour, removed from the ice bath, diluted with ethyl acetate, washed with water, followed by saturated sodium chloride, and then the organic layer was dried over sodium sulfate. The title compound was purified by flash chromatography using a 20–80% gradient of ethyl acetate/hexane.

Example 18

3'-O-t-Butyldimethylsilyl-5'-deoxy-5'-formyl thymidine

3'-O-t-Butyldimethylsilyl-5'-deoxy-5'-hydroxymethyl thymidine was oxidized to the title aldehyde using the same procedure as described for 3'-O-t-butyl-dimethylsilyl thymidine 4'-aldehyde in Example 11.

Example 19

3'-O-t-Butyldimethylsilyl-5'-deoxy-5'-carbethoxyethyl thymidine

To a stirred solution of 3'-O-t-butyldimethylsilyl-5'-carbethoxymethylene-5'-deoxy-thymidine (4.24 g, 10 mmol) in ethyl acetate was added 200 mg of 10% Pd/C under nitrogen atmosphere. The nitrogen gas was removed by vacuum and hydrogen was introduced. This procedure was repeated twice, and stirring was continued under atmospheric pressure of hydrogen for 16 hours. The catalyst was filtered over a celite pad, and the solvent was removed in vacuo. The title compound was crystallized from hexane/ethyl acetate. The title compound was obtained in 95% yield.

Example 20

5'-O-Dimethoxytrityl-3'-acetoxymethyl-3'-deoxy-thymidine

To a solution of 5'-O-dimethoxytrityl-3'-hydroxymethyl-3'-deoxy-thymidine in 20 ml of methylene chloride was added a catalytic amount of dimethylamino-pyridine and excess acetic anhydride. After 1 hour, the reaction mixture was diluted with ethyl acetate, washed with aqueous sodium bicarbonate solution, followed by brine, and the organic layer was dried over sodium sulfate. The title compound was purified by flash chromatography using 25% ethyl acetate/hexane.

Example 21

5'-O-Dimethoxytrityl-3'-methylene-3'-deoxy-thymidine

The title compound was prepared according to the method described by M. Sharma and M Bobek (*Tetrahedron Letters:* 5839–5842, 1990).

Example 22

5'-O-Dimethoxytrityl-3'-hydroxymethyl-3'-deoxy-thymidine

To a solution of 5'-O-dimethoxytrityl-3'-methylene-3'-deoxy-thymidine (200 mg) in 5 ml of methylene chloride at −23° C. was added a 1M solution of borane in THF (2.5 eq.) with stirring. After 1 hour, additional 1M borane in THF (1.5 eq.) was added and the mixture was stirred for 2 hours. The reaction mixture was quenched with a mixture of 0.5M $NaOH-H_2O_2$ and stilled for 15 minutes. The desired product was extracted with ethyl acetate, washed with water, then with brine and the organic layer was dried over sodium sulfate. The title compound was purified by flash chromatography using 90% ethyl acetate/hexane.

Example 23

5'-O-Dimethoxytrityl-3'-formyl-3'-deoxy-thymidine

To a solution of 5'-O-dimethoxytrityl-3'-hydroxymethyl-3'-deoxy-thymidine (215 mg, 0.39 mmol) in 4 ml of methylene chloride was added Dess-Martin Periodinate (245 mg, 1.5 eq.) at 0° C., and the mixture was stirred for 30 minutes. A solution of aqueous 10% sodium hydrogen thiosulfate (3 ml) was added to the above mixture and stirred for 5 minutes. The resulting mixture was diluted with ethyl acetate and washed with water, followed by brine, and the organic layer was dried. The solvent was removed in vacuo, and crude aldehyde was dissolved in 20 ml of chloroform. A drop of DBU was added, and the resulting reaction mixture was stirred for 6 hours. The title compound was purified by flash chromatography using 5% methanol/methylene chloride.

Example 24

3'-O-t-butyldimethylsilyl-5'-aminomethyl-5'-deoxythymidine

To a stirred solution of 3'-O-t-butyldimethylsilyl-5'-deoxy-5'-carboxymethyl thymidine (400 mg) in 10 ml of dry toluene was added triethylamine (1.1 eq.) and diphenyl phosphoryl azide (1.1 eq.), and the mixture was heated to 60° C. with stirring for 40 minutes. An excess of benzyl alcohol was added to the mixture, and stirring was continued for 4 hours. The carbamate was purified by flash chromatography using 5% methanol/methylene chloride. The carbamate (300 mg) was dissolved in 5 ml of ethyl acetate, and 30 mg of $Pd(OH)_2$ was added to the solution. The resulting mixture was stirred under an atmosphere of hydrogen for 12 hours. The catalyst was filtered, and the title compound was purified by flash chromatography using a 10–30% gradient of methanol/methylene chloride.

We claim:

1. A compound having the structural formula

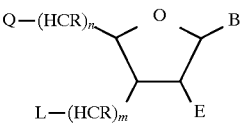

Formula I or a salt thereof, wherein:

Q is selected from the group consisting of H, NHZ, Z, SZ,CHO, COOR, halogen, phosphonium salt and phosphonate;

L is selected from the group consisting of SZ, CHO, COOR, phosphonium salt and phosphonate;

Q-(HCR)$_n$- can also be replaced independently by:

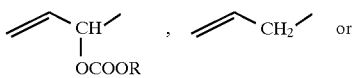

L-(HCR)$_m$- can also be replaced independently by:

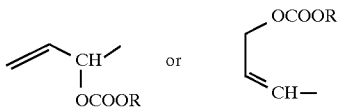

each R is independently selected from the group consisting of H, lower alkyl, lower alkenyl, and acyl;
each Z is independently selected from the group consisting of H, lower alkyl, lower alkenyl, aryl, acyl, and protecting groups for O-, S-, and N-;
each E is independently selected from the group consisting of H, and OZ;
m is 0 or an integer from 1 to 4;
n is an integer from 1 to 5; and
each B is independently selected from the group consisting of adenine, cytosine, guanine, thymine and uracil or a modification thereof that does not substantially interfere with the affinity of an oligonucleoside or chimeric oligonucleotide analog for its antisense counterpart wherein the bases of the antisense counterparts are selected from the group consisting of adenine, cytosine, guanine, thymine and uracil.

2. The compound of claim 1

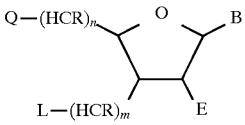

Formula I wherein:

Q is selected from the group consisting of H, NHZ, SZ, COOR, halogen, phosphonium salt and phosphonate;
L is selected from the group consisting of SZ, CHO, COOR, phosphonium salt and phosphonate;
each Z is independently selected from the group consisting of H, lower alkyl, lower alkenyl, aryl, acyl, and protecting groups for S-, and N-; and
E is H.

3. The compound of claim 1, wherein Q is COOR, is 2, and m is 0.

* * * * *